United States Patent [19]  [11] 3,968,102
Suehiro et al.  [45] July 6, 1976

[54] S-SUBSTITUTED-2-THIOADENOSINES

[75] Inventors: Hideo Suehiro; Kiyomi Kikugawa, both of Kokubunji; Motonobu Ichino, Mitaka; Tokuro Nakamura, Mitaka, all of Japan

[73] Assignee: Kohjin Co., Ltd., Tokyo, Japan

[22] Filed: Apr. 16, 1975

[21] Appl. No.: 568,491

[30] Foreign Application Priority Data
Apr. 18, 1974 Japan.............................. 49-42718
Apr. 19, 1974 Japan.............................. 49-43430

[52] U.S. Cl............................. 260/211.5 R; 424/180
[51] Int. Cl.²......................................... C07H 19/16
[58] Field of Search............................. 260/211.5 R

[56] References Cited
UNITED STATES PATENTS
3,752,805  8/1973  Maguire et al............... 260/211.5 R
3,819,612  6/1974  Imai et al..................... 260/211.5 R Primary Examiner—Johnnie R. Brown
Attorney, Agent, or Firm—Sughrue, Rothwell, Mion, Zinn & Macpeak

[57] ABSTRACT
S-Substituted-2-thioadenosines represented by the formula (I):

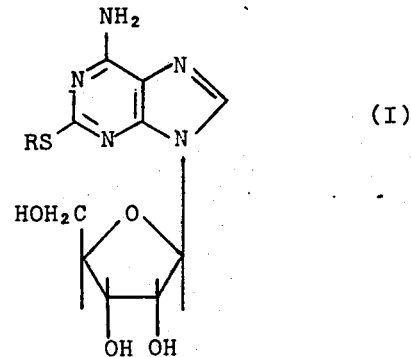

wherein R is as defined hereinafter, useful as a platelet aggregation inhibitor and a coronary vasodilator.

18 Claims, No Drawings

S-SUBSTITUTED-2-THIOADENOSINES

BACKGROUND OF THE INVENTION

1. FIELD OF THE INVENTION

This invention relates to novel S-substituted-2-thioadenosines useful as a platelet aggregation inhibitor and a coronary vasodilator.

2. DESCRIPTION OF THE PRIOR ART

It is well known that a certain type of S-substituted-2-thioadenosines exhibit a vasodilating activity as reported in M. H. Maguire et al., *Journal of Medicinal Chemistry*, Vol. 14, p. 415 (1971); J. A. Argus et al., *British Journal Of Pharmacology*, Vol. 41, p. 592 (1971); and R. Einstein et al., *European Journal of Pharmacology*, Vol. 19, p. 246 (1972). Also, it is well known that some S-substituted-2-thioadenosines possess a platelet aggregation inhibitory activity as reported in G. V. R. Born et al., *Nature*, Vol. 205, p. 678 (1965); F. Michael et al., *Nature*, Vol. 222, p. 1073 (1969); and M. A. Packham et al., *American Journal of Physiology*, Vol. 223, p. 419 (1972). Typical examples of such S-substituted-2-thioadenosines are 2-methylthioadenosine-5'-monophosphate disclosed in U.S. Pat. No. 3,781,274 and 2-lower-alkylthioadenosines disclosed in U.S. Pat. No. 3,752,805. However, the 2-methylthioadenosine-5'-monophosphate exhibits only a weak platelet aggregation inhibitory activity and the 2-lower-alkylthioadenosines have almost no platelet aggregation inhibitory activity.

Recently, a series of S-substituted-2-thioadenosines having improved platelet aggregation inhibitory activities and coronary vasodilating activities has been found as disclosed in U.S. Pat. Application Ser. Nos. 378,116, filed on July 10, 1973, now U.S. Pat. No. 3,919,194, 378,117, filed on July 10, 1973, now U.S. Pat. No. 3,910,883 and 371,340, filed on June 19, 1973, now U.S. Pat. No. 3,910,884.

SUMMARY OF THE INVENTION

The present invention provides a novel class of S-substituted-2-thioadenosines having improved platelet aggregation inhibitory activities and coronary vasodilating activities.

More specifically, this invention provides S-substituted-2-thioadenosines represented by the formula (I):

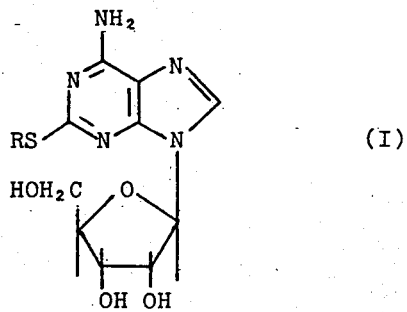

wherein R represents a straight or branched chain alkyl group having 1 to 10 carbon atoms which is substituted with at least one hydroxyl or carboxyl group; a straight or branched chain alkenyl group having 2 to 5 carbon atoms which is substituted with at least one hydroxyl or carboxyl group; a cyclohexyl group which is substituted with at least one hydroxyl or carboxyl group; a substituted or unsubstituted phenyl or naphthyl group wherein the substituent of the phenyl or naphthyl group is selected from the group consisting of an alkyl group having 1 to 4 carbon atoms, an alkoxy group having 1 to 4 carbon atoms, a halogen atom, a nitro group, a hydroxyl group, a carboxyl group and an amino group; a 5- or 6-membered heterocyclic group containing 1 to 3 hetero atoms selected from the group consisting of N, S and O which may be substituted with an alkyl group having 1 to 4 carbon atoms, a nitro group, a hydroxyl group, a carboxyl group or an amino group; a 9- or 10-membered condensed heterocyclic group having 1 to 4 hetero atoms selected from the group consisting of N, S and O which may be substituted with a nitro group, a hydroxyl group or an amino group; an adamantyl group; or a 2-norbornyl group.

DETAILED DESCRIPTION OF THE INVENTION

The term "straight or branched chain alkyl group having 1 to 10 carbon atoms which is substituted with at least one hydroxyl or carboxyl group" used for R designates groups such as 2-hydroxyethyl, 3-hydroxypropyl, 2,3-dihydroxypropyl, 2-hydroxypropyl, 4-hydroxybutyl, 6-hydroxyhexyl, carboxymethyl, 1-carboxyethyl, 1-carboxypentyl, 1-carboxyheptyl, 5-carboxypentyl, 1-carboxy-2-methylpropyl, 2-carboxyethyl, 1-(carboxymethyl)propyl, 1-(carboxymethyl)ethyl, 1-carboxy-1-methylethyl, 10-carboxydecyl, 1-carboxybutyl, 1-carboxynonyl, 1-carboxyhexyl, 1-carboxydecyl, 1,2-dicarboxyethyl and like groups.

The term "straight or branched chain alkenyl group having 2 to 5 carbon atoms which is substituted with at least one hydroxyl or carboxyl group" used for R designates groups such as (E)-3-carboxy-2-butenyl, (E)-3-hydroxymethyl-2-butenyl and like groups.

The term "cyclohexyl group which is substituted with at least one hydroxyl or carboxyl group" designates groups such as trans-2-hydroxycyclohexyl, trans-2-carboxycyclohexyl, trans-4-carboxycyclohexyl and like groups.

The term "substituted or unsubstituted phenyl or naphthyl group" used for R designates groups such as phenyl, 1-naphthyl, 2-naphthyl, o-, m- or p-tolyl, p-tert-butylphenyl, o-, m- or p-hydroxyphenyl, o-, m- or p-methoxyphenyl, 2-methyl-4-fluorophenyl, o-, m- or p-carboxyphenyl, o-, m- or p-aminophenyl, p-chlorophenyl, 2,4-, 2,5-, 3,4-, 3,5-, or 2,6-xylyl, 2-amino-5-methylphenyl, 2-amino-4-methylphenyl, 4-amino-2-methylphenyl, 4-amino-3-methylphenyl, o-, m- or p-nitrophenyl, 2-hydroxy-5-tert-butylphenyl, 4-hydroxy-3-methylphenyl, 4-hydroxy-2-methylphenyl, 2-hydroxy-5-nitrophenyl, 3-nitro-4-hydroxyphenyl, 2-isopropyl-5-methylphenyl, 2-amino-3,5-dinitrophenyl, 3-carboxy-4-hydroxyphenyl, 4-carboxy-3-hydroxyphenyl, 2,4-dihydroxy-5-carboxyphenyl, p-cumenyl, 4-carboxy-2-methyl phenyl, 2-amino-5-nitrophenyl, 5-nitro-2-methylphenyl, o-, m- or p-fluorophenyl, 2-amino-4-chlorophenyl, 6-hydroxy-2-naphthyl, 2-hydroxy-1-naphthyl, 2-methyl-1-naphthyl, 4-methyl-1-naphthyl, 4-amino-1-naphthyl, 3-nitro-2-naphthyl and like groups.

The terms "5- or 6-membered heterocyclic group" and "9- or 10-membered condensed heterocyclic group" designate groups such as 2-pyridyl, 3-pyridyl, 4-pyridyl, 3-hydroxy-2-pyridyl, 2-pyrimidinyl, 4-hydroxy-2-pyrimidinyl, 4-hydroxy-6-propyl-2-pyrimidinyl, 2-thienyl, 2-furyl, 3-furyl, 5-carboxy-2-furyl, 3-indolyl, 5-indolyl, 3-quinolyl, 2-quinolyl, 6-quinolyl, 4-isoquinolyl, 1-methyl-2-imidazolyl, 2-benzimidazolyl, 5-nitro-2-benzimidazolyl, 5-amino-2-benzimidazolyl, 2-purinyl, 6-purinyl, 8-purinyl, 2-amino-6-hydroxy-8-purinyl, 6,8-dihydroxy-2-purinyl, 2-thiazolinyl, 2-thiazolyl, 5-nitro-2-thiazolyl, 2-benzothiazolyl, 6-amino-2-benzothiazolyl, 6-nitro-2-benzothiazolyl, 1,3,4-thiadiazol-2-yl, 5-amino-1,3,4-thiadiazol-2-yl, 1H-1,2,4-triazol-3-yl, 4-hydroxy-2-pteridinyl, 2-benzoxazolyl and like groups.

The term "adamantyl group" used herein includes 1-adamantyl and 2-adamantyl groups.

The term "amino group" used herein designates an unsubstituted amino group, i.e., an -NH₂ group.

The alkyl group having 1 to 4 carbon atoms as substituents on the phenyl, naphthyl or heterocyclic group includes methyl, ethyl, n-propyl, isopropyl, n-butyl, sec-butyl and t-butyl groups.

The alkoxy group having 1 to 4 carbon atoms as substituents on the phenyl or naphthyl group includes methoxy, ethoxy, n-propoxy, isopropoxy, n-butoxy, sec-butoxy and tert-butoxy groups.

The halogen atom as substituents on the phenyl or naphthyl group includes fluorine, chlorine, bromine and iodine atoms.

A preferred class of the S-substituted-2-thioadenosines of this invention is that having the formula (I) above wherein R represents (1) a mono- or di-hydroxyalkyl group or a mono- or di-carboxylalkyl group having 1 to 7 carbon atoms in the alkyl moiety which can be a straight or branched chain; (2) a monohydroxyalkenyl group or a mono-carboxyalkenyl group having 2 to 5 carbon atoms in the alkenyl moiety which can be a straight or branched chain; (3) a 2-hydroxy-, 4-hydroxy, 2-carboxy- or 4-carboxy-cyclohexyl group; (4) a phenyl group, a naphthyl group, an o- or p-monosubstituted, or o- and p-di-substituted phenyl group or a mono- or di-substituted-1 or 2-naphthyl group wherein the substituent of the phenyl or naphthyl group is selected from the group consisting of an alkyl group having 1 to 4 carbon atoms, an alkoxy group having 1 to 2 carbon atoms, a halogen atom, a nitro group, a hydroxyl group, a carboxyl group and an amino group; (5) a substituted or unsubstituted 5- or 6-membered heterocyclic group selected from the group consisting of pyridyl, pyrimidinyl, imidazolyl, thienyl, furyl, thiazolyl, thiadiazolyl, thiazolinyl and triazolyl group wherein the substituent is selected from the group consisting of an alkyl group having 1 to 4 carbon atoms, a nitro group, a hydroxyl group, an amino group and a carboxyl group, or a substituted or unsubstituted 9- or 10-membered condensed heterocyclic group selected from the group consisting of indilyl, quinolyl, isoquinolyl, benzimidazolyl, purinyl, benzothiazolyl, pteridinyl and benzoxazolyl groups wherein the substituent is selected from the group consisting of a nitro group, an amino group and a hydroxyl group; or (6) a 1- or 2-adamantyl group or a 2-norbornyl group.

The most preferred class of the S-substituted-2-thioadenosines of this invention is that having the formula (I) above wherein R represents (1) a mono- or di-hydroxyalkyl group or a mono- or di-carboxylalkyl group having 1 to 7 carbon atoms in the alkyl moiety which can be a straight or branched chain; (2) an (E)-3-carboxy-2-butenyl group; (3) a trans-2-hydroxy-, trans-4-hydroxy-, trans-2-carboxy- or trans-4-carboxy-cyclohexyl group; (4) a phenyl group, a naphthyl group, an o- or p-mono- substituted, or o- and p-di-substituted phenyl group wherein the substituent is selected from the group consisting of an alkyl group having 1 to 4 carbon atoms, a halogen atom, a nitro group, a hydroxyl group, a carboxyl group and an amino group, or a substituted 1- or 2-naphthyl group wherein the substituent is selected from the group consisting of a hydroxy group, a methyl group, an amino group and a nitro group; (5) a substituted or unsubstituted 2-pyridyl, 2-pyrimidinyl, 2-imidazolyl, 2-thienyl, 2-furyl, 2-thiazolyl, 2-thiadiazolyl, 2-thiazolinyl, or 3-triazolyl wherein the substituent is selected from the group consisting of an alkyl group having 1 to 3 carbon atoms, a nitro group, a hydroxyl group, an amino group and a carboxyl group, and a substituted or unsubstituted 2-benzoxazolyl, 2-benzimidazolyl, 2-benzothiazolyl, 3-quinolyl, 3-indolyl or 8purinyl group wherein the substituent is selected from the group consisting of a hydroxyl group, an amino group and a nitro group; or (6) a 1-adamantyl, 2-adamantyl or 2-norbornyl group.

Representative compounds of the present invention having the above formula (I) are:
2-(β-Hydroxyethyl)thioadenosine,
2-(γ-Hydroxypropyl)thioadenosine,
2-Phenylthioadenosine,
2-(o-Tolyl)thioadenosine,
2-(p-Nitrophenyl)thioadenosine,
2-(β-Adamantyl)thioadenosine,
2-(β-Pyridyl)thioadenosine,
2-(β-Norbornyl)thioadenosine,
2-(α-Carboxyethyl)thioadenosine,
2-Carboxymethylthioadenosine,
2-(α-Carboxypentyl)thioadenosine,
2-(2-Hydroxycyclohexyl)thioadenosine,
2-(1-Naphthyl)thioadenosine,
2-(3-Quinolyl)thioadenosine, and
2-(3-Indolyl)thioadenosine.

The S-substituted-2-thioadenosines of this invention represented by the formula (I) can be conveniently prepared by any of the following alternative procedures.

Process 1

This process comprises reacting 2-chloroadenosine represented by the formula (II):

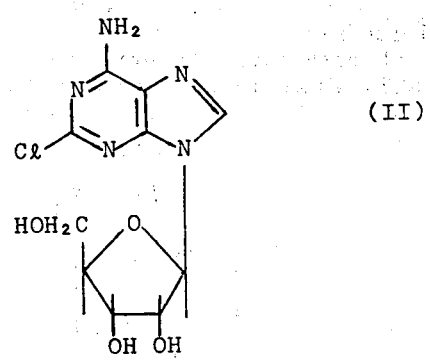

with a thiol compound represented by the formula (III):

wherein R is as defined above, to produce the S-substituted-2-thioadenosines of the formula (I).

Process 2

This process comprises reacting 2-thioadenosine represented by the formula (IV):

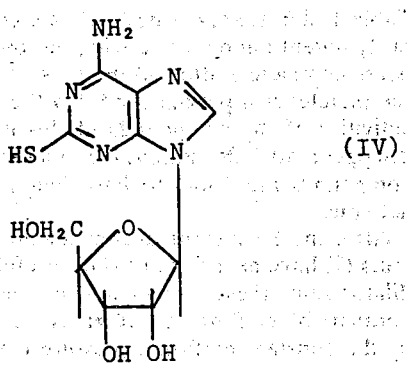

with a halide represented by the formula (V):

wherein R is as defined above and X represents a halogen atom selected from the group consisting of chlorine, bromine and iodine atoms, to produce the S-substituted-2-thioadenosines of the formula (I).

The starting material, 2-chloroadenosine of the formula (II) used in the above Process 1 can be obtained in high yield from 6-chloroguanosine or a 2',3',5'-triacyl-6-chloroguanosine as disclosed in Japanese Patent Application OPI No. 48,496/1973. That is, 6-chloroguanosine or a 2',3',5'-triacyl-6-chloroguanosine, e.g., 2',3',5'-triacetyl-6-chloroguanosine, is first reacted with sodium nitrite and hydrochloric acid in ice-water and thereafter the reaction mixture is neutralized with, for example, aqueous ammonia. The resulting reaction mixture is then extracted with a solvent such as methylene chloride and the extract containing 2,6-dichloropurine riboside is treated without isolation of the riboside, with a methanolic solution saturated with anhydrous ammonia gas and the mixture is allowed to react at a temperature of about 100°C for about 5 hours in a sealed tube to obtain the desired 2-chloroadenosine of the formula (II) in about 60% yield. The preparation of the starting material of the formula (II) will be hereinafter described in greater detail in Reference Example 1.

In carrying out Process 1 of the present invention, the 2-chloroadenosine of the formula (II) obtained as above is reacted with a thiol compound of the formula (III) in water or an organic solvent. The solvent used for the above reaction can be any type of solvents which are chemically inert to 2-chloroadenosine of the formula (II) or the thiol compounds of the formula (III), but from the standpoint of yield of the desired products, N,N-dimethylformamide, hexamethylphosphoramide, dimethylsulfoxide and the like can be preferably used. The reaction is preferably conducted in the presence of an alkali as an acid acceptor for the hydrogen chloride formed during the reaction. Examples of suitable alkalis which can be used as an acid acceptor are alkali metals such as sodium metal, potassium metal and the like, alkali metal hydroxides such as sodium hydroxide, potassium hydroxide and the like, and tertiary amines such as triethylamine, 1,8-diazabicyclo[5.4.0]und-7-ene (DBU) and the like. These acid acceptors can be used in an equimolar amount to a molar excess, preferably 1 to 10 moles per mole of the 2-chloroadenosine starting material. The reaction between the 2-chloroadenosine and the thiol compound can be conducted using an equimolar amount to a molar excess, preferably 1 to 10 moles of the thiol compound per mole of 2-chloroadenosine, at a temperature of about 0° to about 200°C. The reaction time varies depending upon the reaction temperature used, but generally ranges from about 0.5 to 100 hours. As is apparent to one skilled in the art, the higher the reaction temperature, the shorter is the reaction time.

The starting material, the 2-thioadenosine of the formula (IV), used in the above Process 2 can be obtained in high yield from 2-chloroadenosine of the formula (II) by the procedure disclosed in Japanese Patent Application OPI No. 52,795/1973. That is, 2-chloroadenosine is reacted with sodium hydrogen sulfide in a solvent such as dimethylformamide at a temperature of about 50°C to 100°C to obtain the desired 2-thioadenosine of the formula (IV) in about 100% yield. The preparation of the starting material of the formula (IV) will be hereinafter described in greater detail in Reference Example 2.

In carrying out the Process 2 of the present invention, the 2-thioadenosine of the formula (IV) obtained as above is reacted with a halide of the formula (V) in water or an organic solvent. The solvent used for the above reaction can be any type of solvent which is chemically inert to the 2-thioadenosine of the formula (IV) and the halide of the formula (V), but the solvent is preferably selected depending on the type of the halide used. That is, when hydroxy- or carboxy-substituted alkylhalides are used as reactants, water or an alcohol such as methanol, ethanol, isopropanol and the like is preferably used as a solvent, and when halides of unsubstituted or substituted phenyl, naphthyl, heterocyclic compounds, polycyclic alkyls are used as reactants, N,N-dimethylformamide, hexamethylphosphoramide, dimethylsulfoxide, etc., is preferably used as a solvent. The reaction is preferably conducted in the presence of an alkali as an acid acceptor for the hydrogen halide formed during the reaction. Examples of suitable alkalis which can be used as an acid acceptor are those described above for Process 1. These acid acceptors can be used in an equimolar amount to a molar excess, preferably 1 to 10 moles per mole of the 2-thioadenosine starting material. The reaction between 2-thioadenosine and the halide can be conducted using an equimolar amount to a molar excess, preferably 1 to 10 moles of the halide per mole of 2-thioadenosine, at a temperature of about 0° to about 200°C. The reaction time varies depending upon the reaction temperature used, but generally ranges from about 0.5 to 100 hours. As is apparent to one skilled in the art, the higher the reaction temperature, the shorter is the reaction time.

The isolation of the product, the S-substituted-2-thioadenosines of the formula (I), from the reaction mixture obtained by either Process 1 or Process 2 above can be accomplished using well known procedures such as crystallization. When the product contains a carboxyl group in the R moiety, the product tends to be crystallized from the reaction mixture in the form of an alkali metal salt of the carboxyl group, e.g., the —COONa or -COOK form where the alkali metal corresponds to that of the alkali used in the reaction. Alternatively, the product can be crystallized by concentrating the reaction mixture and suspending the concentrate in water to cause crystallization, or by adjusting the reaction mixture to a pH of about 1 to 7 with an acid such as hydrochloric acid, concentrating the resulting mixture, extracting the concentrate with an organic solvent such as ethanol, methanol, ethyl acetate and the like, and crystallizing the product with water, an alcohol such as methanol, ethanol, isopropanol or a mixture thereof.

As was described previously, the S-substituted-2-thioadenosines of the formula (I) possess a platelet aggregation inhibitory activity. The platelet aggregation inhibitory activity of representative compounds of the formula (I) were determined in terms of the percent inhibitory activity against $10^{-5}M$ adenosine-5'-diphosphate (hereinafter referred to as "ADP")-induced or collagen-induced platelet aggregation in rabbit platelet-rich plasma according to the procedure described by G. V. R. Born and M. J. Cross in *Journal of Physiology*, Vol. 168, p. 178 (1963). The results obtained are shown in Table 1 below where the activity was evaluated after a 3 minute incubation of a mixture of the platelet aggregation inhibitor and the rabbit platelet-rich plasma.

Table 1 above, adenosine used as a control exhibits a fairly potent inhibitory activity, but this activity disappears completely after 60 minutes of incubation with the platelet-rich plasma used. On the other hand, the activities of the compounds of this invention do not disappear after 60 minutes of incubation and these compounds are found to have long-lasting inhibitory activities.

Also, the S-substituted-2-thioadenosines of the formula (I) have been found to be a useful coronary vasodilator since these compounds markedly increase the coronary blood flow after administration as determined by the constant perfusion pressure method of the left circumflex coronary artery in dogs.

Further, the S-substituted-2-thioadenosines of the formula (I) exhibit a low toxicity in mammals and a therapeutic index which is superior to that of the well-known closely-related compounds.

The S-substituted-2-thioadenosines of this invention

TABLE 1

| Compound | Concentration | Solvent | Inhibition (%) $10^{-5}M$ ADP-Induced Aggregation | Collagen-Induced Aggregation |
|---|---|---|---|---|
| 2-(β-Hydroxyethyl)-thioadenosine | $10^{-4}M$ | PSS* | 52 | 30 |
| 2-(γ-Hydroxypropyl)-thioadenosine | $10^{-4}M$ | PSS | 58 | 52 |
| 2-Phenylthioadenosine | $10^{-4}M$ | DMSO** | 98 | 82 |
| 2-Phenylthioadenosine | $10^{-5}M$ | DMSO | 62 | 58 |
| 2-(o-Tolyl)thioadenosine | $10^{-5}M$ | DMSO | 61 | 57 |
| 2-(p-Nitrophenyl)-thioadenosine | $10^{-4}M$ | DMSO | 92 | 81 |
| 2-(β-Adamantyl)-thioadenosine | $10^{-4}M$ | DMSO | 95 | 72 |
| 2-(β-Adamantyl)-thioadenosine | $10^{-5}M$ | DMSO | 72 | 61 |
| 2-(β-Pyridyl)thioadenosine | $10^{-4}M$ | PSS | 61 | 52 |
| 2-(β-Norbornyl)-thioadenosine | $10^{-4}M$ | DMSO | 89 | 69 |
| 2-(β-Norbornyl)-thioadenosine | $10^{-5}M$ | DMSO | 62 | 51 |
| Adenosine | $10^{-4}M$ | PSS | 80 | 71 |
| Adenosine | $10^{-4}M$ | DMSO | 76 | 68 |
| Adenosine | $10^{-5}M$ | PSS | 58 | 51 |
| Ammonium Adenosine-5'-monophosphate | $10^{-4}M$ | PSS | 5 | — |
| Ammonium 2-Methylthioadenosine-5'-monophosphate | $10^{-4}M$ | PSS | 35 | — |
| 2-Methylthioadenosine | $10^{-4}M$ | PSS | 12 | 25 |
| 2-Propylthioadenosine | $10^{-4}M$ | PSS | 16 | — |
| 2-Thioadenosine | $10^{-4}M$ | PSS | 10 | 36 |

*PSS: Physiological saline solution
**DMSO: Dimethylsulfoxide

The above results indicate that the S-substituted-2-thioadenosines of this invention exhibit an excellent platelet aggregation inhibitory activity against ADP-induced or collagen-induced aggregation.

2-Thioadenosine, which is used as the starting material for the synthesis of the S-substituted-2-thioadenosines of the formula (I), exhibits only a weak inhibitory activity in both ADP-induced and collagen-induced platelet aggregation as disclosed in *Journal of Medicinal Chemistry*, Vol. 16, No. 12, 1381 ~ 1388 (1973).

As can be understood from the results shown in can be administered to humans via various routes such as oral, rectal, intravenous and intramuscular administrations, preferably via an oral administration, for alleviating or treating cardiac failure or thrombosis. For example, these compounds can be administered orally to an adult (weighing 50 to 60 kg on the average) in single or multiple dosages at a dose level of about 0.1 to 100 mg per day.

The compounds of the formula (') can be administered alone or in combination with conventional pharmaceutical excipients, disintegrating agents, binders, lubricants, solubilizing agents, emulsifying agents, suspending agents, stabilizers, buffering agents, isotonic agents, preservatives, etc., in dosage forms such as powders, tablets, capsules, granules, pills, suppositories, liquids preparations such as suspensions, emulsions, syrups, elixirs and the like, injections and the like which are all well known in the art.

For oral administration, the S-substituted-2-thioadenosines of this invention can be conveniently formulated into tablets containing about 1 to 20 mg of the active ingredient with diluents or excipients such as lactose, cellulose powder and the like together with pharmaceutically acceptable lubricants, etc. The tablets may be coated with, for example, a sugar coating.

The present invention is further illustrated in greater detail by the following Reference Examples and Examples, but these examples are given for illustrative purposes only and are not to be construed as limiting the invention. Examples 1 to 7 illustrate the preparation of the S-substituted-2-thioadenosine derivatives of the formula (I) by Process 1 and Examples 8 to 17 illustrate the preparation of S-substituted-2-thioadenosine derivatives of the formula (I) by Process 2. Unless otherwise indicated, all percents, ratios, parts and the like are by weight.

REFERENCE EXAMPLE 1

100 g of 2′,3′,5′-triacetyl-6-chloroguanosine was dissolved in 400 ml of concentrated hydrochloric acid and, after the mixture was cooled to 0°C, a solution of 20 g of sodium nitrite dissolved in 50 ml of water was then added slowly to the mixture. The resulting mixture was allowed to react for 30 minutes, neutralized with concentrated aqueous ammonia and extracted with 2 l of methylene chloride. The extract was dried over anhydrous sodium sulfate and concentrated. The concentrate thus-obtained was dissolved in 300 ml of saturated methanolic ammonia and the mixture was allowed to react at a temperature of 100°C for 5 hours in a sealed tube. The reaction mixture was then concentrated to dryness and the residue was crystallized from water to obtain 42.3 g (60% yield) of 2-chloroadenosine. Recrystallization from water was repeated to obtain crystals having the following constant physical properties.
Melting Point: 161° ~ 162°C (with decomposition)
U.V. Absorption Spectrum:

| | | |
|---|---|---|
| $\lambda_{max}^{pH\ 1}$ | 265.5 nm | ($\epsilon$: 16660) |
| $\lambda_{min}^{pH\ 1}$ | 231 nm | ($\epsilon$: 3170) |
| $\lambda_{max}^{pH\ 7}$ | 265 nm | ($\epsilon$: 17400) |
| $\lambda_{min}^{pH\ 7}$ | 230 nm | ($\epsilon$: 3050) |
| $\lambda_{max}^{pH\ 13}$ | 265.5 nm | ($\epsilon$: 17300) |
| $\lambda_{min}^{pH\ 13}$ | 233 nm | ($\epsilon$: 4120) |

Specific Rotation: $[\alpha]_D^{25°}$ −69.0° (c: 0.34 in $H_2O$)
$R_f$ Values in Paper Chromatography:
0.50 (solvent: n-butanol-water, 84:16 by volume)
0.75 (solvent: $NH_3$-water, pH 10)
NMR Spectrum (solvent, $d_6$-DMSO)
δ: 3.6 ($C_5'$ H),
3.8~4.2 overlapping triplet ($C_4'$H and $C_3'$ H or $C_2'$ H),
4.50 triplet ($C_3'$ H or $C_2$ H),
4.8~5.6 ($C_3'$ OH, $C_2'$ OH and $C_5'$ OH),
5.85 doublet ($C_1'$ H),
7.80 (6-$NH_2$),
8.4 ($C_8H$).
Elemental Analysis: Calcd. for $C_{10}H_{12}O_4N_5Cl.1/2\ H_2O$ (%): C: 38.7, H: 4.2, N: 22.5, Cl: 11.41. Found (%): C: 39.18, H: 4.18, N: 22.67, Cl: 11.55.

The above analytical values were quite consistent with those given in the literature.

REFERENCE EXAMPLE 2

2.0 g of 2-chloroadenosine was dissolved in a solution of 20 ml of anhydrous hydrogen sulfide and 1.5 g of sodium metal in 80 ml of dimethylformamide, and the mixture was allowed to react at a temperature of 80°C for 5 hours under anhydrous conditions. The reaction mixture was then diluted with 80 ml of water and neutralized with acetic acid followed by concentration. The resulting concentrate was dissolved in 75 ml of a mixture of n-butanol and water (2:1 by volume), and 25 ml of acetic acid was added to the solution. After allowing the mixture to cool, the precipitated crystals were filtered to obtain 21 g (100% yield) of crude 2-thioadenosine. The product thus-obtained was dissolved in dilute aqueous ammonia and adjusted to a pH of 4 with acetic acid to obtain pure 2-thioadenosine having a melting point of 196° ~ 199°C (with decomposition).
U.V. Absorption Spectrum:

| | |
|---|---|
| $\lambda_{max}^{pH\ 1}$ | 238.5 nm ($\epsilon$: 13800), 295 nm ($\epsilon$: 18400) |
| $\lambda_{max}^{pH\ 3.2}$ | 289 nm ($\epsilon$: 18300) |
| $\lambda_{max}^{pH\ 13}$ | 243 nm ($\epsilon$: 19100), 283 nm ($\epsilon$: 14000) |
| $\lambda_{min}^{pH\ 1}$ | 220.5 nm ($\epsilon$: 9400), 256.5 nm ($\epsilon$: 2800) |
| $\lambda_{min}^{pH\ 3.2}$ | 251.5 nm ($\epsilon$: 3100) |
| $\lambda_{min}^{pH\ 13}$ | 227 nm ($\epsilon$: 12500), 259 nm ($\epsilon$: 7100) | pKa: 7.8
Specific Rotation: $[\alpha]_D^{25°}$ −43.6° (c: 0.5 in dimethylsulfoxide)
Elemental Analysis: Calcd. for $C_{10}H_{13}O_4N_5S.H_2O$ (%): C: 37.89, H: 4.77, N: 22.09, S: 10.12 Found (%): C: 37.67, H: 4.88, N: 21.82, S: 10.22

The NMR spectrum of the product was found to be quite consistent with its structure.

EXAMPLE 1

Preparation of 2-(β-Hydroxyethyl)thioadenosine 200 mg of 2-chloroadenosine was suspended in 5 ml of N,N-dimethylformamide, and 23 mg of sodium metal was then added to the suspension to dissolve the 2-chloroadenosine. 120 mg of β-mercaptoethanol was then added to the solution and the mixture was heated under refluxing for 10 hours. The resulting reaction mixture was concentrated to dryness and the residue was washed with petroleum ether and crystallized from water to obtain 160 mg (72% yield) of 2-(β-hydroxyethyl)thioadenosine having a melting point of 212° ~ 213°C (with decomposition).
Elemental Analysis: Calcd. for $C_{12}H_{17}O_5N_5S$ (%): C: 41.97, H: 4.99, N: 20.40 Found (%): C: 42.00, H: 4.96, N: 20.31

EXAMPLE 2

Preparation of 2-(α-Carboxyethyl)thioadenosine 200 mg of 2-chloroadenosine was suspended in 5 ml of N,N-dimethylformamide, and 23 mg of sodium metal was then added to the suspension to dissolve the 2-chloroadenosine. 140 mg of α-mercaptopropionic acid was then added to the solution and the mixture was heated under refluxing for 10 hours. The resulting reaction mixture was extracted with petroleum ether. The aqueous layer was then concentrated to a small volume and ethanol was added to the concentrate to obtain 146 mg (66% yield) of the sodium salt of 2-(α-carboxyethyl)thioadenosine having a melting point above 270°C.

Elemental Analysis: Calcd. for $C_{13}H_{16}O_6N_5S\cdot Na$ (%): C: 39.69, H: 4.10, N: 17.81 Found (%): C: 39.67, H: 4.02, N: 17.87

EXAMPLE 3

Preparation of 2-Carboxymethylthioadenosine 200 mg of 2-chloroadenosine was suspended in 5 ml of N,N-dimethylformamide, and 23 mg of sodium metal was then added to the suspension to dissolve the 2-chloroadenosine. 800 mg of mercaptoacetic acid was then added to the solution and the mixture was heated under refluxing for 10 hours. The resulting reaction mixture was concentrated under reduced pressure to dryness and the residue was washed with petroleum ether and dissolved in a small amount of water. The resulting aqueous solution was neutralized to obtain crystalline 2-carboxymethylthioadenosine. Recrystallization from water yielded 213 mg (90% yield) of pure product having a melting point of 236° ~ 238°C (with decomposition).

Elemental Analysis: Calcd. for $C_{12}H_{15}O_6N_5S\cdot 1/4\ H_2O$ (%): C: 39.83, H: 4,32, N: 19.36 Found (%): C: 39.95, H: 4.18, N: 19.22

EXAMPLE 4

Preparation of 2-Phenylthioadenosine 310 mg of 2-chloroadenosine was suspended in 8 ml of N,N-dimethylformamide, and 150 mg of sodium metal was then added to the suspension to dissolve the 2-chloroadenosine. 880 mg of benzenethiol was then added to the solution and the mixture was heated under refluxing for 7 hours. The resulting reaction mixture was neutralized with hydrochloric acid and concentrated to dryness. The resulting residue was washed with petroleum ether and crystallized from 50% aqueous ethanol to obtain 210 mg (56% yield) of 2-phenylthioadenosine having a melting point of 267° ~ 268.5°C (with decomposition).

Elemental Analysis: Calcd. for $C_{16}H_{17}O_4N_5S$ (%): C: 51.19, H: 4.56, N: 18.66 Found (%): C: 51.07, H: 4.57, H: 18.56

EXAMPLE 5

Preparation of 2-(o-Tolyl)thioadenosine 310 mg of 2-chloroadenosine was suspended in 8 ml of N,N-dimethylformamide, and 150 mg of sodium metal was then added to the suspension to dissolve the 2-chloroadenosine. 995 mg of o-toluenethiol was then added to the solution and the mixture was heated under refluxing for 7 hours. The resulting reaction mixture was neutralized with hydrochloric acid and concentrated to dryness. The resulting residue was washed with petroleum ether and crystallized from 50% aqueous ethanol to obtain 226 mg (58% yield) of 2-(o-tolyl)thioadenosine having a melting point above 270°C (with decomposition).

Elemental Analysis: Calcd. for $C_{17}H_{19}O_4N_5S$ (%): C: 52.43, H: 4.92, N: 17.98 Found (%): C: 52.36, H: 4.87, N: 18.07

EXAMPLE 6

Preparation of 2-(β-Pyridyl)thioadenosine 310 mg of 2-chloroadenosine was suspended in 8 ml of N,N-dimethylformamide, and 150 mg of sodium metal was then added to the suspension to dissolve the 2-chloroadenosine. 880 mg of 2-pyridinethiol was then added to the solution and the mixture was heated under refluxing for 7 hours. The resulting reaction mixture was concentrated to dryness, and the residue was washed with petroleum ether and crystallized from water to obtain 300 mg (80% yield) of 2-(β-pyridyl)thioadenosine having a melting point of 212° ~ 214°C (with decomposition).

Elemental Analysis: Calcd. for $C_{15}H_{16}O_4N_6S$ (%): C: 47.87, H: 4.28, N: 22.33 Found (%): C: 47.98, H: 4.22, N: 22.12

EXAMPLE 7

Preparation of 2-(β-Adamantyl)thioadenosine 200 mg of 2-chloroadenosine was suspended in 8 ml of N,N-dimethylformamide, and 150 mg of sodium metal was then added to the suspension to dissolve the 2-chloroadenosine. 300 mg of 2-adamantanethiol as then added to the solution and the mixture was heated under refluxing for 18 hours. The resulting reaction mixture was concentrated to dryness and the resulting residue was washed with petroleum ether and crystallized from water to obtain 244 mg (85% yield) of 2-(β-adamantyl)thioadenosine having a melting point above 270°C (with decomposition).

Elemental Analysis: Calcd. for $C_{20}H_{27}O_4N_5S$ (%): C: 55.41, H: 6.28, N: 16.16 Found (%): C: 55.43, H: 6/20, N: 16.31

In the same manner as described in the foregoing Examples 1 to 7, but using each of the following thiol compounds of the formula (III), the S-substituted-2-thioadenosines of the formula (I) having each of the following substituents were prepared:

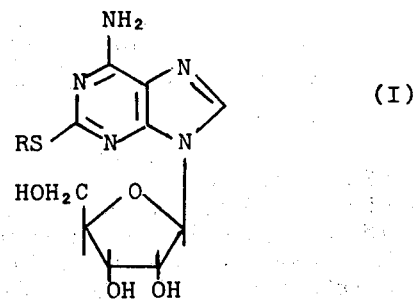

(I)

| Compound No. | Thiol Compound of Formula (III) | R-Substituent in the S-Substituted-2-Thioadenosine (I) |
|---|---|---|
| 1 | 3-Mercapto-1,2-Propanediol | HOCH$_2$—CHCH$_2$—<br>　　　　　$\vert$<br>　　　　　OH |
| 2 | trans-2-Mercaptocyclohexane-carboxylic acid | 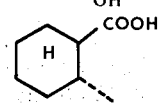 |

-continued

| Compound No. | Thiol Compound of Formula (III) | R-Substituent in the S-Substituted-2-Thioadenosine (I) |
|---|---|---|
| 3 | 2-Naphthalenethiol | 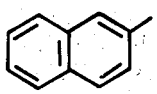 |
| 4 | p-tert-Butylbenzenethiol | 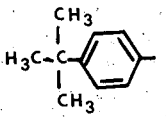 |
| 5 | p-Chlorobenzenethiol | 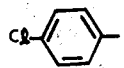 |
| 6 | 2-Mercapto-3-pyridinol | 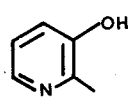 |
| 7 | 1-Methyl-2-imidazolethiol | 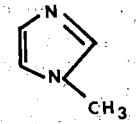 |
| 8 | 2-Mercapto-1,3,4-thiadiazole | 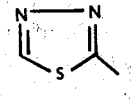 |
| 9 | 2-Thiazolinethiol | 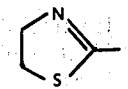 |
| 10 | 5-Nitro-2-benzimidazolethiol | 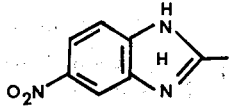 |
| 11 | 2-Benzoxazolethiol | 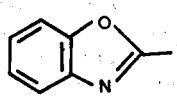 |
| 12 | 2-Benzothiazolethiol | 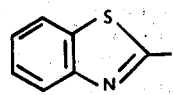 |
| 13 | 3-(1H)-1,2,4-Triazolethiol | 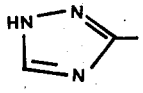 |

EXAMPLE 8

Preparation of 2-(β-Hydroxyethyl)thioadenosine 200 mg of 2-thioadenosine was dissolved in 8.1 ml of 0.25N sodium hydroxide solution and 790 mg of ethylenebromohydrin was added to the solution. The resulting mixture was then allowed to react overnight at room temperature (i.e., about 20° ~ 30°C) while stirring, and the reaction mixture was neutralized with hydrochloric acid. The mixture was then concentrated and the resulting residue was washed with petroleum ether and crystallized from water to obtain 174.1 mg (80.5% yield) of 2-(β-hydroxyethyl)thioadenosine having a melting point of 211° ~ 212.5°C (with decomposition).

Elemental Analysis: Calcd. for $C_{12}H_{17}O_5N_5S$ (%): C: 41.97, H: 4.99, N: 20.40 Found (%): C: 41.71, H: 4.93, N: 20.24

EXAMPLE 9

Preparation of 2-(γ-Hydroxypropyl)thioadenosine 200 mg of 2-thioadenosine was dissolved in 8.1 ml of 0.25N sodium hydroxide solution and 880 mg of 3-bromo-1-propanol was added to the solution. The resulting mixture was then allowed to react overnight at room temperature while stirring, and the reaction mixture was neutralized with hydrochloric acid. The mixture was then concentrated and the resulting residue was washed with petroleum ether and crystallized from ethanol to obtain 140 mg (61% yield) of 2-(γ-hydroxypropyl)thioadenosine having a melting point of 117° ~ 119°C.

Elemental Analysis: Calcd. for $C_{13}H_{19}O_5N_5S$ (%): C: 43.69, H: 5.36, N: 19.60 Found (%): C: 43.58, H: 5.32, N: 19.48

EXAMPLE 10

Preparation of 2-Carboxymethylthioadenosine 200 mg of 2-thioadenosine was dissolved in 8.1 ml of 0.25N sodium hydroxide solution and 880 mg of monobromoacetic acid was added to the solution. The resulting mixture was then allowed to react overnight at room temperature while stirring, and the precipitated crystals were filtered and recrystallized from water to obtain 200 mg (88% yield) of 2-carboxymethylthioadenosine having a melting point of 236°~ 238°C (with decomposition).

Elemental Analysis: Calcd. for $C_{12}H_{15}O_6N_5S \cdot 1/4 H_2O$ (%): C: 39.83, H: 4.32, N: 19.36. Found (%): C: 39.89, H: 4.20, N: 19.37.

EXAMPLE 11

Preparation of 2-(α-Carboxyethyl)thioadenosine 317 mg of 2-thioadenosine was dissolved in 0.52 ml of 4N sodium hydroxide solution and 2.48 ml of water was added to the solution. Thereafter, 964 mg of α-bromopropionic acid was added to the solution and the resulting mixture was allowed to react for 48 hours at room temperature while stirring. The resulting reaction mixture was extracted with petroleum ether and the aqueous layer was concentrated to a small volume. Ethanol was then added to the concentrate to obtain 280 mg (71% yield) of the sodium salt of 2-(α-carboxyethyl)thioadenosine having a melting point above 270°C.

Elemental Analysis: Calcd. for $C_{13}H_{16}O_6N_5S \cdot Na$ (%): C: 39.69, H: 4.10, N: 17.81 Found (%): C: 39.78, H: 4.08, N: 17.74

EXAMPLE 12

Preparation of 2-(α-Carboxypentyl)thioadenosine 317 mg of 2-thioadenosine was dissolved in 2.1 ml of 4N sodium hydroxide solution and 3 ml of water was added to the solution. Thereafter, 1230 mg of 2-bromohexanoic acid was added to the solution and the resulting mixture was allowed to react for 48 hours at a temperature of 50°C. The resulting reaction mixture was extracted with petroleum ether and the aqueous layer was concentrated to a small volume. Ethanol was then added to the concentrate to obtain 340 mg (78% yield) of the sodium salt of 2-(α-carboxypentyl)thioadenosine having a melting point above 270°C.

Elemental Analysis: Calcd. for $C_{16}H_{22}O_6N_5S \cdot Na$ (%): C: 44.13, H: 5.09, N: 16.08 Found (%) C: 44.10, H: 5.18, N: 15.99

EXAMPLE 13

Preparation of 2-Phenylthioadenosine 317 mg of 2-thioadenosine was suspended in 3 ml of N,N-dimethylformamide, and 23 mg of sodium metal was added to the suspension to dissolve the 2-thioadenosine. 260 mg of iodobenzene was then added to the solution and the mixture was heated at the reflux temperature for 24 hours. The resulting reaction mixture was concentrated to dryness, and the residue was washed with petroleum ether and crystallized from 50% aqueous ethanol to obtain 233 mg (62% yield) of 2-phenylthioadenosine having a melting point of 266 ~ 268°C (with decomposition).

Elemental Analysis: Calcd. for $C_{16}H_{17}O_4N_5S$ (%): C: 51.19, H: 4.56, N: 18.66 Found (%): C: 51.21, H: 4.54, N: 18.49

EXAMPLE 14

Preparation of 2-(p-Nitrophenyl)thioadenosine 317 mg of 2-thioadenosine was suspended in 3 ml of N,N-dimethylformamide, and 23 mg of sodium metal was added to the suspension to dissolve 2-thioadenosine. 255 mg of p-bromonitrobenzene was then added to the solution and the mixture was heated at the reflux temperature for 18 hours. The resulting reaction mixture was concentrated to dryness, and the residue was crystallized from 50% aqueous ethanol to obtain 350 mg (83% yield) of 2-(p-nitrophenyl)thioadenosine having a melting point of 205 ~ 207°C (with decomposition).

Elemental Analysis: Calcd. for $C_{16}H_{16}O_6N_6S$ (%): C: 45.71, H: 3.84, N: 19.99 Found (%): C: 45.62, H: 3.82, N: 19.86

EXAMPLE 15

Preparation of 2-(β-Adamantyl)thioadenosine 317 mg of 2-thioadenosine was suspended in 3 ml of N,N-dimethylformamide, and 23 mg of sodium metal was added to the suspension to dissolve the 2-thioadenosine. 270 mg of 2-bromoadamantane was then added to the solution and the mixture was heated under refluxing for 18 hours. The resulting reaction mixture was concentrated to dryness, and the residue was washed with petroleum ether and crystallized from 50% aqueous ethanol to obtain 360 mg (83% yield) of 2-(β-adamantyl)thioadenosine having a melting point above 270°C (with decomposition).

Elemental Analysis: Calcd. for $C_{20}H_{27}O_4N_5S$ (%): C: 55.41, H: 6.28, N: 16.16 Found (%): C: 55.30, H: 6.24, N: 16.05

EXAMPLE 16

Preparation of 2-(β-Pyridyl)thioadenosine 317 mg of 2-thioadenosine was suspended in 3 ml of N,N-dimethylformamide, and 23 mg of sodium metal was then added to the suspension to dissolve the 2-thioadenosine. 200 mg of 2-bromopyridine was then added to the solution and the mixture was heated under refluxing for 8 hours. The resulting reaction mixture was concentrated to dryness and the residue was washed with petroleum ether and crystallized from water to obtain 290 mg (77% yield) of 2-(β-pyridyl)thioadenosine having a melting point of 212° ~ 213°C (with decomposition).

Elemental Analysis: Calcd. for $C_{15}H_{16}O_4N_6S$ (%): C:

47.87, H: 4.28, N: 22.33 Found (%): C: 47.93, H: 4.19, N: 22.31

EXAMPLE 17

Preparation of 2-(β-Norbornyl)thioadenosine 317 mg of 2-thioadenosine was suspended in 3 ml of N,N-dimethylformamide, and 23 mg of sodium metal was added to the suspension to dissolve the 2-thioadenosine. 220 mg of exo-2-bromonorbornane was then added to the solution and the mixture was heated under refluxing for 24 hours. The resulting reaction mixture was concentrated to dryness and the residue was washed with petroleum ether and crystallized from 50% aqueous ethanol to obtain 340 mg (87% yield) of 2-(β-norbornyl)thioadenosine having a melting point of 266 ~ 268°C (with decomposition).

Elemental Analysis: Calcd. for $C_{17}H_{23}O_4N_5S$ (%): C: 51.89, H: 5.89, N: 17.80 Found (%): C: 51.91, H: 5.93, N: 17.72

In the same manner as described in the foregoing Examples 8 to 17, but using each of the following halides of the formula (V), the S-substituted-2-thioadenosines of the formula (I) having each of the following substituents were prepared:

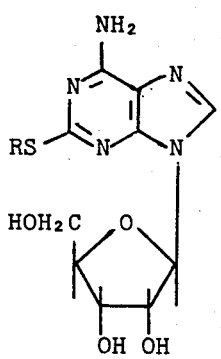

(I)

| Compound No. | Halide of Formula (V) | R-Substituent in the S-Substituted-2-Thioadenosine of Formula (I) |
|---|---|---|
| 1 | 2-Bromooctanoic acid | HOOC\CH— / CH₃(CH₂)₅ |
| 2 | trans-2-Bromocyclohexanol | cyclohexyl with OH, H --- |
| 3 | trans-4-Bromocyclohexane-carboxylic acid | HOOC—cyclohexyl—H --- |
| 4 | γ-Bromotiglic acid | H₃C\C=C/C'₂— / HOOC \H |
| 5 | p-Bromotoluene | H₃C—C₆H₄— |
| 6 | p-Bromophenol | HO—C₆H₄— |
| 7 | 2-Bromo-5-fluorotoluene | F—C₆H₃(CH₃)— |
| 8 | p-Bromobenzoic acid | HOOC—C₆H₄— |
| 9 | o-Bromoaniline | o-NH₂-C₆H₄— |
| 10 | p-Bromoanisole | H₃CO—C₆H₄— |
| 11 | 6-Bromo-2-naphthol | HO-naphthyl— |
| 12 | 2-Bromopyrimidine | pyrimidin-2-yl |
| 13 | 2-Iodothiophene | thien-2-yl |
| 14 | 5-Bromo-2-furancarboxylic acid | HOOC-furyl— |
| 15 | 2-Bromo-5-nitrothiazole | O₂N-thiazol-2-yl |
| 16 | 3-Bromoquinoline | quinolin-3-yl |
| 17 | 3-Bromoindole | indol-3-yl (NH) |
| 18 | 8-Bromoguanine | guanin-8-yl |
| 19 | Monochloroacetic acid | HOOC.CH₂— |
| 20 | 1-Bromoadamantane | adamantyl |

While the invention has been described in detail and with reference to specific embodiments thereof, it will be apparent to one skilled in the art that various changes and modifications can be made therein without departing from the spirit and scope thereof.

What is claimed is:

1. A compound of the formula

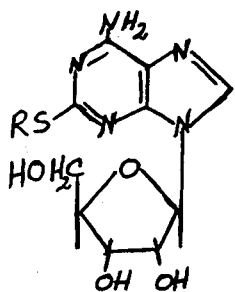

wherein R is a mono- or di-hydroxyalkyl group or a mono- or dicarboxylalkyl group having 1 to 7 carbon atoms in the alkyl moiety which can be a straight or branched chain; a mono-hydroxyalkenyl group or a mono-carboxyalkenyl group having 2 to 5 carbon atoms in the alkenyl moiety which can be a straight or branched chain; a 2-hydroxy-, 4-hydroxy-, 2-carboxy- or 4-carboxy-cyclohexyl group; a phenyl group; a naphthyl group; an o- or p-mono-substituted, or o- or p-di-substituted phenyl group or a mono- or di-substituted-2-naphthyl group wherein the substituent of the phenyl or naphthyl group is selected from the group consisting of an alkyl group having 1 to 4 carbon atoms, an alkoxy group having 1 or 2 carbon atoms, a halogen atom, a nitro group, a hydroxyl group, a carboxyl group and an amino group; a substituted or unsubstituted 5- or 6- membered heterocyclic group selected from the group consisting of pyridyl, pyrimidinyl, imidazolyl, thienyl, furyl, thiazolyl, thiadiazolyl, thiazolinyl and triazolyl groups wherein the substituent is selected from the group consisting of an alkyl group having 1 to 4 carbon atoms, a nitro group, a hydroxyl group, an amino group and a carboxyl group; a substituted or unsubstituted 9- or 10-membered condensed heterocyclic group selected from the group consisting of indolyl, quinolyl, isoquinolyl, benzimidazolyl, purinyl, benzothiazolyl, pteridinyl and benzoxazolyl groups wherein the substituent is selected from the group consisting of a nitro group, an amino group and a hydroxyl group; a 1- or 2-adamantyl group; or a 2-norbornyl group.

2. The S-substituted-2-thioadenosines according to claim 1, wherein R represents a mono- or di-hydroxyalkyl group or a mono- or di-carboxyalkyl group having 1 to 7 carbon atoms in the alkyl moiety which can be a straight or branched chain; an (E)-3-carboxy-2-butenyl group; a trans-2-hydroxy-, trans-4-hydroxy-, trans-2-carboxy- or trans-4-carboxy-cyclohexyl group; a phenyl group; a naphthyl group; or o- or p-mono-substituted, or o- and p-di-substituted phenyl group wherein the substituent is selected from the group consisting of an alkyl group having 1 to 4 carbon atoms, a halogen atom, a nitro group, a hydroxyl group, a carboxyl group and an amino group; a substituted 1-or 2-naphthyl group wherein the substituent is selected from the group consisting of a hydroxyl group, a methyl group, an amino group and a nitro group; a substituted or unsubstituted 2-pyridyl, 2-pyrimidinyl, 2-imidazolyl, 2-thienyl, 2-furyl, 2-thiazolyl, 2-thiadiazolyl, 2-thiazolinyl or 3-triazolyl wherein the substituent is selected from the group consisting of an alkyl group having 1 to 3 carbon atoms, a nitro group, a hydroxyl group, an amino group and a carboxyl group; a substituted or unsubstituted 2-benzoxazolyl, 2-benzimidazolyl, 2-benzothiazolyl, 3-quinolyl, 3-indolyl or 8-purinyl group wherein the substituent is selected from the group consisting of a hydroxyl group, an amino group and a nitro group; or a 1-adamantyl, 2-adamantyl or 2-norbornyl group.

3. The compound according to claim 1, wherein R is β-hydroxyethyl, γ-hydroxypropyl, carboxymethyl, α-carboxyethyl, α-carboxypentyl, 2-hydroxycyclohexyl, phenyl, o-tolyl, p-nitrophenyl, 1-naphthyl, β-pyridyl, 3-quinolyl, 3-indolyl, β-adamantyl or β-norbornyl.

4. 2-(β-Hydroxyethyl)lthioadenosine according to claim 1.

5. 2-(γ-Hydroxypropyl) thioadenosine according to claim 1.

6. 2-Phenylthioadenosine according to claim 1.

7. 2-(o-Tolyl)thioadenosine according to claim 1.

8. 2-(p-Nitrophenyl)thioadenosine according to claim 1.

9. 2-(β-Adamantyl)thioadenosine according to claim 1.

10. 2-(β-Pyridyl)thioadenosine according to claim 1.

11. 2-(β-Norbornyl)thioadenosine according to claim 1.

12. 2-(α-Carboxyethyl)thioadenosine according to claim 1.

13. 2-Carboxymethylthioadenosine according to claim 1.

14. 2-(α-Carboxypentyl)thioadenosine according to claim 1.

15. 2-(2-Hydroxycyclohexyl)thioadenosine according to claim 1.

16. 2-(1-Naphthyl)thioadenosine according to claim 1.

17. 2-(3-Quinolyl)thioadenosine according to claim 1.

18. 2-(3-Indolyl)thioadenosine according to claim 1.

* * * * *